United States Patent
Sutton et al.

(10) Patent No.: US 8,608,810 B2
(45) Date of Patent: Dec. 17, 2013

(54) HAIR COLORANT COMPOSITIONS COMPRISING 3-AMINO-2,6-DIMETHYLPHENOL AND 1,4-PHENYLENEDIAMINE-TYPE DEVELOPERS, METHODS, AND KITS COMPRISING THE COMPOSITIONS

(71) Applicant: The Procter & Gamble Company, Cincinnati, OH (US)

(72) Inventors: Richard Matthew Charles Sutton, Cincinnati, OH (US); Bryan Patrick Murphy, Loveland, OH (US); Margaret Ann Popp, West Chester, OH (US); Stephen Robert Schofield, London (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/851,825

(22) Filed: Mar. 27, 2013

(65) Prior Publication Data

US 2013/0255004 A1    Oct. 3, 2013

Related U.S. Application Data

(60) Provisional application No. 61/616,071, filed on Mar. 27, 2012.

(51) Int. Cl.
*A61Q 5/10* (2006.01)

(52) U.S. Cl.
USPC ............... 8/405; 8/406; 8/408; 8/410; 8/412; 8/435

(58) Field of Classification Search
USPC ...................... 8/405, 406, 408, 410, 412, 435
See application file for complete search history.

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 3,712,790 A | 1/1973 | Kalopissis | |
| 3,730,677 A | 5/1973 | Kalopissis | |
| 3,929,404 A | 12/1975 | Kalopissis | |
| 3,955,918 A | 5/1976 | Lang | |
| 3,977,825 A | 8/1976 | Kalopissis | |
| 4,007,747 A | 2/1977 | Kalopissis | |
| 4,008,043 A | 2/1977 | Kalopissis | |
| 4,008,999 A | 2/1977 | Kalopissis | |
| 4,213,758 A | 7/1980 | Lieske | |
| 4,330,291 A | 5/1982 | Bugaut | |
| 4,692,166 A | 9/1987 | Junino | |
| 4,985,955 A | 1/1991 | Grollier | |
| 5,207,798 A | 5/1993 | Cotteret | |
| 5,279,619 A | 1/1994 | Cotteret | |
| 5,364,414 A | 11/1994 | Lang | |
| 5,391,206 A | 2/1995 | Cotteret | |
| 5,500,022 A | 3/1996 | Cotteret | |
| 5,595,573 A | 1/1997 | Audousset | |
| 5,683,474 A | 11/1997 | Cotteret | |
| 7,985,266 B2 | 7/2011 | Zhang | |
| 2007/0006397 A1 | 1/2007 | Schmenger | |
| 2007/0017040 A1 | 1/2007 | Pasquier | |
| 2007/0067926 A1* | 3/2007 | Schmitt et al. ................... 8/405 |
| 2011/0035885 A1 | 2/2011 | Zhang | |

FOREIGN PATENT DOCUMENTS

| | | |
|---|---|---|
| CA | 2576189 A1 | 6/2007 |
| DE | 102004058061 A1 | 6/2006 |
| EP | 1518539 A1 | 3/2005 |
| GB | 1267635 A | 3/1972 |
| GB | 1483861 A | 8/1977 |
| GB | 2211517 A | 7/1989 |
| GB | 2224518 A | 5/1990 |
| WO | WO0193819 A1 | 12/2001 |
| WO | WO0206207 A2 | 1/2002 |
| WO | WO0210118 A1 | 2/2002 |
| WO | WO0226201 A2 | 4/2002 |
| WO | WO0232379 A2 | 4/2002 |
| WO | WO02083090 A2 | 10/2002 |
| WO | WO03041671 A2 | 5/2003 |
| WO | WO2006048069 A1 | 5/2006 |

OTHER PUBLICATIONS

U.S. Appl. No. 13/851,835, filed Mar. 27, 2013, Sutton et al.
Encyclopedia of Chemical Technology, Kirk-Othmer, Third Edition, 1982, vol. 3, pp. 896-900.
Encyclopedia of Chemical Technology, Kirk-Othmer, Third Edition, 1982, vol. 15, pp. 439-458.
Polymers in Nature by E. A. MacGregor and C. T. Greenwood, published by John Wiley & Sons, Chapter 6, pp. 240-328,1980.
Handbook of Surfactants by M. R. Porter, published by Blackie & Son (Glasgow and London), 1991, pp. 116-178.

* cited by examiner

*Primary Examiner* — Eisa Elhilo
(74) *Attorney, Agent, or Firm* — James T. Fondriest

(57) ABSTRACT

A hair colorant composition comprises 3-amino-2,6-dimethylphenol in combination with a second dye coupler selected from the group consisting of 2,6-dihydroxyethylaminotoluene, 2,6-diaminopyridine and a developer selected from the group consisting of 2-methyl-1,4-benzenediamine, 2-methyl-1,4-benzenediamine sulfate salt, p-phenylenediamine, p-toluenediamine, hydroxyethyl-p-phenylenediamine, N,N-bis(hydroxyethyl)-p-phenylenediamine, 2-methoxymethyl-1,4-benzenediamine. A kit for coloring hair comprises the hair colorant composition. A method of treating hair comprises applying the hair colorant composition to hair.

17 Claims, No Drawings

HAIR COLORANT COMPOSITIONS COMPRISING 3-AMINO-2,6-DIMETHYLPHENOL AND 1,4-PHENYLENEDIAMINE-TYPE DEVELOPERS, METHODS, AND KITS COMPRISING THE COMPOSITIONS

FIELD OF THE INVENTION

The present invention relates generally to hair colorant compositions and, more specifically, to oxidative hair colorant compositions containing a combination of a 1,4-phenylenediamine-type developer with couplers comprising 3-amino-2,6-dimethylphenol, methods for treating hair with the oxidative hair colorant compositions, and hair-coloring kits comprising the oxidative hair colorant compositions.

BACKGROUND OF THE INVENTION

The permanent alteration of the color of keratinous fibers, in particular human hair, by the application of hair dyes is well known. Oxidative hair dye precursors, i.e., developers (also called primary intermediates) and couplers diffuse into the hair through the cuticle and into the cortex. The precursors combine in the presence of an oxidizing agent, such as hydrogen peroxide, to form larger-sized dye molecules that result in a visual color of the hair ("end hair color") that is distinct from the color of the hair before coming into contact with the precursors and oxidizing agent. Different combinations of developers and couplers produce different shades of hair color when combined with the oxidizing agent. The end hair color is not easily predicted given the complex chemical process that occurs to achieve an end hair color.

Permanent hair colorant formulations should produce end hair colors that are stable for at least 4 to 6 weeks. Additionally, the end hair color should exhibit good washfastness, good lightfastness, fastness to rubbing, as well as sufficient resistance with respect to perspiration. Preferably, it should be possible to produce a broad palette of different color shades by combining suitable developers and couplers. Hair colorant formulations also should be stable, for example, in terms of shelf life, ability to retain color benefits after storage (i.e., stability of the developers and couplers), and chemical stability both after mixing and during application to hair.

Hair colorant formulations generally provide acceptable and immediate results. However, achieving both desired shade (hue) and depth of shade (chroma) remains challenging, particularly for hair colorant formulations that impart reddish colors to the hair. To achieve desirable shades in the red area, 5-amino-2-methylphenol (AHT):

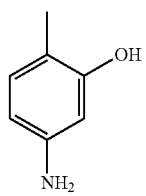

(AHT)

is one common example of a suitable coupler, to be used by itself or in a mixture with other couplers, in combination with one or more suitable developer or developers. For example, when AHT is used as a coupler in combination with 4-aminophenol and a standard oxidant system such as ammonium hydroxide and hydrogen peroxide, red shades may be achieved. Nevertheless, the red shades may fail to provide the desirable red hue and chroma and, thereby, the hair colorant formulation may fall short of producing the desired end hair color.

GB Pat. No. 1,229,517 discusses a class of couplers having formula (A):

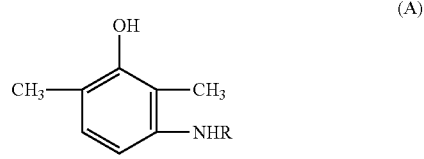

(A)

in which R of formula (A) is hydrogen, lower alkyl or hydroxyalkyl, acyl, of an N-alkylated or unsubstituted amino lower alkyl or carbamylmethyl group. The couplers are exemplified in combination with p-toluenediamine (2-methyl-1,4-benzenediamine) to produce colors such as violet, blue-grey, eggplant, violet-blue, reddish blond, and bluish black on white hair.

U.S. Pat. Appl. Pub. No. 2007/0067926 discusses agents for oxidative coloring of keratin fibers, in which 2-amino-5-ethylphenol is combined with at least one m-aminophenol. Exemplified compositions each comprise the 2-amino-5-ethylphenol and the m-aminophenol as couplers, in combination with one or more developers.

There remains an ongoing need for additional hair colorant compositions that can provide desirable red shades, particularly when used with other oxidant systems, i.e., ammonium carbonate, hydrogen peroxide, and, optionally, a radical scavenger and/or chelant. There remain further needs for hair colorant compositions that deliver not only redder shades with increased chromaticity, but also increased stability and shelf life.

SUMMARY OF THE INVENTION

Embodiments described herein relate to a hair colorant composition comprising (a) a first coupler consisting of 3-amino-2,6-dimethylphenol; (b) a second coupler selected from the group consisting of 2,6-dihydroxyethylaminotoluene, 2,6-diaminopyridine, cosmetically acceptable salts of any of these, and mixtures of at least two of these; (c) a developer selected from the group consisting of 2-methyl-1, 4-benzenediamine (PTD); 2-methyl-1,4-benzenediamine sulfate salt (DTS); p-phenylenediamine (PPD); hydroxyethyl-p-phenylenediamine; N,N-bis(hydroxyethyl)-p-phenylenediamine; 2-methoxymethyl-1,4-benzenediamine (MBB); cosmetically acceptable salts of any of these; and mixtures comprising at least two of these; and (d) an oxidizing agent.

Further embodiments described herein relate to a method of treating hair. The method comprises contacting hair with a hair colorant composition resulting from mixing a first composition and a second composition comprising an oxidizing agent. The first composition comprises a first coupler consisting of 3-amino-2,6-dimethylphenol; a second coupler selected from the group consisting of 2,6-dihydroxyethylaminotoluene, 2,6-diaminopyridine, cosmetically acceptable salts of any of these, and mixtures of at least two of these; and a developer selected from the group consisting of 2-methyl-1,4-benzenediamine (PTD); 2-methyl-1,4-benzenediamine sulfate salt (DTS); p-phenylenediamine (PPD), hydroxyethyl-p-phenylenediamine, N,N-bis(hydroxyethyl)-p-phenylenediamine, 2-methoxymethyl-1,4-benzenediamine (MBB), cosmetically acceptable salts of any of these, and mixtures comprising at least two of these.

Still further embodiments described herein relate to a hair coloring kit comprising an individually packaged oxidizing component and an individually packaged dye component. The individually packaged oxidizing component comprises an oxidizing agent. The individually packaged dye component may comprise a first coupler consisting of 3-amino-2,6-dimethylphenol; a second coupler selected from the group consisting of 2,6-dihydroxyethylaminotoluene, 2,6-diaminopyridine, cosmetically acceptable salts of any of these, and mixtures of at least two of these; and a developer selected from the group consisting of 2-methyl-1,4-benzenediamine (PTD); 2-methyl-1,4-benzenediamine sulfate salt (DTS); p-phenylenediamine (PPD), hydroxyethyl-p-phenylenediamine, N,N-bis(hydroxyethyl)-p-phenylenediamine, 2-methoxymethyl-1,4-benzenediamine (MBB), cosmetically acceptable salts of any of these, and mixtures comprising at least two of these.

These and other features, aspects, and advantages of the present invention will become better understood with reference to the following detailed description and appended claims.

DETAILED DESCRIPTION OF THE INVENTION

As used herein, the term "hair" in the context of the oxidative hair colorant compositions and their uses according to various embodiments, encompasses without limitation keratin-containing fibers that may be regarded as "living," i.e., on a living body, or as "non-living," i.e., in a wig, hairpiece, or other aggregation of non-living keratinous fibers. Though mammalian hair is preferred, human hair being a particular example thereof, it will be understood that also wool, fur, and other keratin-containing fibers are suitable substrates for the compositions described herein.

As used herein, the term "cosmetically acceptable salts" means salts which are suitable for use in contact with the skin or hair of humans and lower animals without undue toxicity, incompatibility, instability, irritation, allergic response, and the like for example chlorides, bromides, sulfates, malates, tartrates, lactates and acetates.

Hair colorant composition comprises (a) a first coupler consisting of 3-amino-2,6-dimethylphenol (MeAHT); (b) a second coupler selected from the group consisting of 2,6-dihydroxyethylaminotoluene, 2,6-diaminopyridine, cosmetically acceptable salts of any of these, and mixtures of at least two of these; (c) a developer selected from the group consisting of 2-methyl-1,4-benzenediamine (PTD), 2-methyl-1,4-benzenediamine sulfate salt (DTS), p-phenylenediamine (PPD), hydroxyethyl-p-phenylenediamine, N,N-bis(hydroxyethyl)-p-phenylenediamine, 2-methoxymethyl-1,4-benzenediamine (MBB), cosmetically acceptable salts of any of these, and mixtures comprising at least two of these; and (d) an oxidizing agent.

The first coupler consists of 3-amino-2,6-dimethylphenol (MeAHT). MeAHT has the formula (I):

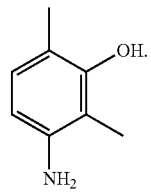

(I)

Based on the weight of the oxidative hair colorant composition, the hair colorant composition may comprise up to about 12% by weight, especially from about 0.001% to about 6%, or from about 0.05% to about 6% by weight, of MeAHT.

The second coupler is selected from the group consisting of 2,6-dihydroxyethylaminotoluene of formula (IIA)

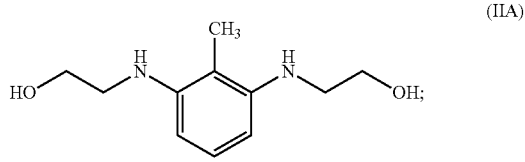

(IIA)

2,6-diaminopyridine of formula (IIB)

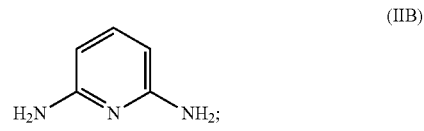

(IIB)

cosmetically acceptable salts of any of these; and mixtures of at least two of these. Based on the weight of the hair colorant composition, the hair colorant composition may comprise up to about 12% by weight, especially from about 0.001% to about 6%, or from about 0.05% to about 6% by weight, of the second coupler. Preferably, the hair colorant composition may comprise a total of up to about 12% by weight, especially from about 0.001% to about 6%, or from about 0.05% to about 6% by weight, of the MeAHT and the second coupler combined.

The developer is selected from the group consisting of 2-methyl-1,4-benzenediamine (PTD), 2-methyl-1,4-benzenediamine sulfate salt (DTS), p-phenylenediamine (PPD), hydroxyethyl-p-phenylenediamine, N,N-bis(hydroxyethyl)-p-phenylenediamine, 2-methoxymethyl-1,4-benzenediamine (MBB), cosmetically acceptable salts of any of these, and mixtures comprising at least two of these. Each of the developers may be described according to formula (III), cosmetically acceptable salts of any of the compounds of formula (III), and mixtures thereof.

Formula (III) is represented as follows:

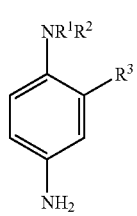

(IV)

where $R^1$ and $R^2$ are independently selected as hydrogen or 2-hydroxyethyl (—CH$_2$CH$_2$OH); $R^3$ is selected from hydrogen, —CH$_3$, —CH$_2$CH$_2$OH, or —CH$_2$OCH$_3$. In one embodiment, $R^1$ and $R^2$ are identical. Examples of compounds having formula (IV) include, but are not limited to, p-phenylenediamine (PPD; wherein $R^1$, $R^2$ and $R^3$ are all selected as hydrogen); p-toluenediamine (PTD; wherein $R^1$ and $R^2$ are selected as hydrogen and $R^3$ is selected as —CH$_3$); hydroxyethyl-p-phenylenediamine (wherein $R^1$ and $R^2$ are selected as hydrogen and $R^3$ is selected as —CH$_2$CH$_2$OH); N,N-bis(hydroxyethyl)-p-phenylenediamine (wherein $R^1$ and $R^2$ are selected as —CH$_2$CH$_2$OH and $R^3$ is selected as hydrogen); and 2-methoxymethyl-1,4-benzenediamine (MBB; wherein $R^1$ and $R^2$ are selected as hydrogen and $R^3$ is selected as —CH$_2$OCH$_3$). An example of a cosmetically acceptable salt of a compounds having formula (IV) includes 2-methyl-1,4-benzenediamine sulfate salt (DTS; sulfate salt of PTD).

Based on the weight of the hair colorant composition, the hair colorant composition may comprise up to 12% by weight, especially from about 0.001% to about 6%, or from about 0.05% to about 6% by weight, of the developer. Preferably, the hair colorant composition may comprise a total of up to about 12% by weight, especially from about 0.001% to about 6%, or from about 0.05% to about 6% by weight, of MeAHT, the second coupler, and the developer combined.

It has been found that the specific combinations of MeAHT, the second coupler, and the developer described above, when incorporated into a hair colorant composition, impart desirably redder shades with higher chromaticity, than comparable compositions including alternate couplers such as AHT. As such, it may be preferable in some embodiments that the oxidative hair colorant composition be devoid of AHT. The term "devoid of AHT" means that no AHT is intentionally added to the oxidative hair colorant composition, such that less than 0.01 wt % by weight of the hair colorant composition, preferably such as 800 ppm or less may be present.

Oxidizing Agent

The hair colorant composition may comprise at least one source of an oxidizing agent. Preferred oxidizing agents for use herein are water soluble peroxygen oxidizing agents. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulfates and the like. These inorganic perhydrate salts may be incorporated as monohydrates, tetrahydrates etc. Alkyl and aryl peroxides, and or peroxidases, oxidase, and uricases and their substrates may also be used. Mixtures of two or more such oxidizing agents can also be used if desired. The oxidizing agents may be provided in aqueous solution or as a powder which is dissolved prior to use. Preferred for use in the hair colorant compositions are hydrogen peroxide, percarbonate, persulfates and combinations thereof.

The oxidizing agent may comprise from about 0.1% to about 20% by weight, preferably from about 1% to about 15% by weight, and more preferably from about 2% to about 10% by weight, most preferably from about 3% to about 6% by weight of the hair colorant composition.

A potential oxidizing agent for use herein is a source of peroxymonocarbonate ions formed in situ from a source of hydrogen peroxide and a hydrogen carbonate ion source. Moreover, this system is also particularly effective in combination with a source of ammonia or ammonium ions. Accordingly, any source of these peroxymonocarbonate ions may be used. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may be used both as an oxidizing agent and as a source of carbonate ions. Preferred sources of carbonate ions, carbamate and hydrocarbonate ions are sodium hydrogen carbonate, potassium hydrogen carbonate, ammonium carbamate, and mixtures thereof.

The oxidative agent may comprise from about 0.1% to about 15% by weight, preferably from about 1% to about 10% by weight, and most preferably from about 1% to about 8% by weight of a hydrogen carbonate ion and from about 0.1% to about 10% by weight, preferably from about 1% to about 7% by weight, and most preferably from about 2% to about 5% by weight of the oxidative agent of a source of hydrogen peroxide.

Optional Additional Dye Components

The hair colorant composition may contain additional dye components that may be selected from those known in the art, for example, one or more direct dyes, one or more oxidative dye precursors, or mixtures thereof.

Optional Direct Dyes

The hair colorant compositions may further comprise compatible direct dyes, in an amount sufficient to provide or enhance coloring, particularly with regard to intensity. Typically, such an amount will range from about 0.05% to about 4%, by weight of the hair colorant composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, Acid Blue 16, Acid Blue 62, Acid Blue 25, Acid Red 4, Basic Dyes such as HC Blue 16, Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino) propyl)-4-methylmorpholin-4-ium-methylsulfate, (E)-1-(2-(4-(4,5-dimethylthiazol-2-yl)diazenyl)phenyl)(ethyl)amino) ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4-a,9,9a,10-tetrahydroanthracen-1-ylamino)-N-propylpropan-1-aminium bromide, Disperse Dyes such as Disperse Red 17, Disperse Violet 1, Disperse Red 15, Disperse Violet 1, Disperse Black 9, Disperse Blue 3, Disperse Blue 23, Disperse Blue 377, Nitro Dyes such as 1-(2-(4-nitrophenylamino) ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene) bis(azanediyl)diethanol, HC Yellow No. 5, HC Red No. 7, HC Blue No. 2, HC Yellow No. 4, HC Yellow No. 2, HC Orange No. 1, HC Red No. 1,2-(4-amino-2-chloro-5-nitrophenylamino)ethanol, HC Red No. 3,4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9,2-chloro-6-(ethylamino)-4-nitrophenol, 6-nitropyridine-2,5-diamine, HC Violet No. 2,2-amino-6-chloro-4-nitrophenol, 4-(3-hydroxypropylamino)-3-nitrophenol, HC Yellow No. 13,6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14, and Natural dyes such as Annato, Anthocyanin, Beetroot, Carotene, Capsanthin, Lycopene, Chlorophyll, Henna, Indigo, Cochineal.

Optional Additional Oxidative Dye Precursors

The hair colorant compositions may include additional oxidative dye compounds in the form of primary intermediates or couplers, herein referred to as oxidative dye precursors. Oxidative dye precursors may be free bases or the cosmetically acceptable salts thereof. It is to be understood that the additional precursors are detailed below only by way of example and are not intended to limit the hair colorant compositions or sub-components such as a tint compositions therein.

Suitable primary intermediates for use in the compositions described herein include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene and mixtures thereof.

Suitable couplers for use in the compositions described herein include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

The total quantity of the additional oxidative dye precursors contained in the hair colorant composition, or sub-component thereof, may be up to about 12% by weight, especially from about 0.05% to about 6% by weight of the hair colorant composition.

Solvent

The hair colorant composition may comprise solvents such as water, lower aliphatic alcohols, for example with 1 to 4 carbon atoms such as ethanol, propanol and isopropanol, aromatic alcohols such as benzyl alcohol and phenoxyethanol or polyols or polyol ethers such as glycerin, and 1,2- and 1,3-propylene glycol, carbitols, 2-butoxyethanol, diethylene glycol, monoethyl ether, monomethyl ether, hexylene glycol, glycerol, ethoxy glycol, butoxydiglycol, ethoxydiglycerol, dipropyleneglycol and polygylcerol. The solvents may be utilized for the hair colorant composition or in sub-components such as in a tint composition or an oxidizing composition in concentrations of from 0.1% to 30% by weight.

pH-Modifying Agents

The hair colorant composition, generally in a tint composition packaged separately from the oxidizing agent (e.g., oxidizing composition), may comprise a pH-modifying agent such as an alkalizing agent.

Any alkalizing agent known in the art may be used such as: alkanolamides, for example monoethanolamine, diethanolamine, triethanolamine, monopropanolamine, dipropanolamine, tripropanolamine, 2-amino-2-methyl-1,3-propanediol, 2-amino-2-methyl-1-prop anol, and 2-amino-2-hydroxymethyl-1,3-propanediol; guanidium salts; and alkali-metal and ammonium hydroxides and carbonates, such as sodium hydroxide and ammonium carbonate. Particularly, preferred alkalizing agents are those which provide a source of ammonium ions.

Any source of ammonium ions is suitable for use herein. Preferred sources of ammonium ions include ammonium chloride, ammonium sulfate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonia, and mixtures thereof.

The hair colorant composition or the tint composition may comprise from about 0.1% to about 10% by weight, such as from about 0.5% to about 5%, such as from about 1% to about 3% of an alkalizing agent, such as a source of ammonium ions.

pH

The hair colorant compositions described above may have a pH of from 7 to 12, preferably from 8 to 11. For embodiments comprising a peroxymoncarbonate ion, the pH is preferably up to and including pH 9.5, more preferably from about 7.5 to about 9.5, even more preferably from about 8.4 to about 9.5, most preferably from about 8.5 to about 9.4, for example, about 9.0 or about 9.3.

Any sub-components of the hair colorant compositions, such as a tint composition or an oxidizing composition, may have a different pH from the hair colorant composition. For example, if the tint composition comprises an alkalizing agent, the tint composition will have an alkaline pH, such as higher than 7. The oxidizing composition may comprise an acidic pH of less than 7.

The pH of the hair colorant compositions can be determined by using either a Mettler Toledo MP220 or a MP225 pH equipment, fitted with a standard laboratory pH electrode. The equipment is calibrated before each use using standard calibration buffers and using the standard calibration procedure.

Optional Chelants

Suitable optional chelants for use in hair colorant compositions are carboxylic acids (in particular aminocarboxylic acids) and phosphonic acids (in particular aminophosphonic acids) and polyphosphoric acids (e.g., linear polyphosphoric acids), including the salts and derivatives of these chelants. Generally, the chelants do not penetrate the hair to any significant extent under typical oxidative hair coloring conditions. As such, the chelants generally do not affect color formation inside the hair.

The hair colorant compositions may comprise from about 0.01% to about 5%, in some embodiments, from about 0.25% to about 3%, in certain embodiments, from about 0.5% to about 1% of chelant, salts thereof, derivatives thereof, or mixtures thereof.

The hair colorant compositions may comprise an aminocarboxylic acid chelant. Aminocarboxylic acid chelants as defined herein are chelants having at least one carboxylic acid moiety (—COOH) and at least one nitrogen atom. Examples of aminocarboxylic acid chelants suitable for use herein include diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), EDDHA (ethylenediamine-N—N'-bis(o-hydroxyphenyl acetic acid)), diaminoalkyldi(sulfosuccinic acids) (DDS), N,N'-bis(2-hydroxybenzyl)ethylenediamine-N,N'-diacetic acid (HBED), salts thereof and derivatives thereof.

Other suitable aminocarboxylic type chelants for use herein are iminodiacetic acid derivatives such as N-2-hydroxyethyl-N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, salts thereof and derivatives thereof. Dipicolinic acid and 2-phosphonobutane-1,2,4-tricarboxylic acid are also suitable.

In further embodiments, the hair colorant compositions may comprise from about 0.1% to about 5% of diethylenetriaminepenta(methylenephosphonic acid) and from about 0.1% to about 5% of ethylenediamine-N,N'-disuccinic acid, and from about 0.1% to about 5% of diethylenetriaminepentaacetic acid. Preferred for use herein is ethylenediamine-N,N'-disuccinic acid (EDDS), derivatives and salts thereof.

The hair colorant compositions may comprise a chelant selected from aminophosphonic acid type chelants, salts thereof, derivatives thereof and mixtures thereof. Aminophosphonic acid type chelants are defined as chelants comprising an aminophosphonic acid moiety (—$PO_3H_2$) or its derivative —$PO_3R^2$ wherein $R^2$ is a $C_1$ to $C_6$ alkyl or aryl radical.

Suitable aminophosphonic acid type chelants for use herein are aminotri-(1-ethylphosphonic acid), ethylenediaminetetra-(1-ethylphosphonic acid), aminotri-(1-propylphosphonic acid), and aminotri-(isopropylphosphonic acid). Preferred chelants for use herein are aminotri-(methylenephosphonic acid), ethylenediaminetetra(methylenephosphonic acid) (EDTMP) and diethylene-triamine-penta-(methylenephosphonic acid) (DTPMP) and mixtures thereof.

Optional Radical Scavenger

The hair colorant compositions may further comprise a source of radical scavenger. As used herein, the term "radical scavenger" refers to a species that can react with a radical, e.g. a carbonate radical, to convert the radical by a series of fast reactions to a less reactive, or unreactive, species. Suitable radical scavengers for use herein may be selected from the classes of alkanolamines, amino sugars, amino acids, esters of amino acids, pyrazolones, such as those discussed in US 2011/0035885A1, and mixtures thereof. Particularly preferred compounds are: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof, 3-carboxy-1H-pyrazol-5-one, 3-carboxy-1-phenyl-pyrazol-5-one, 3-carboxy-1-(4-sulfophenyl)-pyrazol-5-one, 3-carboxy-1-(4-carboxyphenyl)-pyrazol-5-one, and mixtures thereof. Especially preferred compounds are glycine, sarcosine, lysine, serine, 2-methoxyethylamine, glucosamine, glutamic acid, morpholine, piperidine, ethylamine, 3-amino-1-propanol, and mixtures thereof.

The hair colorant compositions may comprise from about 0.1% to about 10% by weight, preferably from about 1% to about 7% by weight of the hair colorant composition of a radical scavenger.

In one embodiment, the radical scavenger may be present at an amount such that the weight ratio of radical scavenger to carbonate ion is from 2:1 to 1:4. The radical scavenger may be selected such that it is not an identical species as the alkalizing agent. According to one embodiment, the radical scavenger may be formed in situ in the hair colorant composition prior to application to the hair fibers.

Optional Conditioning Agent

The hair colorant composition may comprise a conditioning agent. Optionally, a separate conditioning composition comprising a conditioning agent may be used after the hair colorant composition. Conditioning agents suitable are selected from silicone materials, aminosilicones, fatty alcohols, polymeric resins, polyol carboxylic acid esters, cationic polymers, insoluble oils and oil derived materials and mixtures thereof. Additional materials include mineral oils and other oils such as glycerin and sorbitol. Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain.

Silicones can be selected from polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain or mixtures thereof. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion.

The conditioning agent generally will be used at levels of from about 0.05% to about 20% by weight of the hair coloring composition or the conditioning composition, such as from about 0.1% to about 15%, such as from about 0.2% to about 10%, such as from about 0.2% to about 2% by weight of the hair coloring composition or the conditioning composition.

Polymer Thickener

According to the present invention, the hair coloring compositions may comprise a polymer thickener, comprising at least one polymer selected from associative polymers, polysaccharides, non-associative polycarboxylic polymers, and mixtures thereof.

As used herein, the expression "associative polymers" means amphiphilic polymers comprising both hydrophilic units and hydrophobic units, for example, at least one C8 to C30 fatty chain and at least one hydrophilic unit. Associative polymers are capable of reversibly combining with each other or with other molecules. Representative associative thickeners that may be used are associative polymers chosen from:

(i) nonionic amphiphilic polymers comprising at least one hydrophilic unit and at least one fatty-chain unit; (ii) anionic amphiphilic polymers comprising at least one hydrophilic unit and at least one fatty-chain unit;

(iii) cationic amphiphilic polymers comprising at least one hydrophilic unit and at least one fatty-chain unit; and (iv) amphoteric amphiphilic polymers comprising at least one hydrophilic unit and at least one fatty-chain unit.

The nonionic amphiphilic polymers comprising at least one fatty chain and at least one hydrophilic unit may, for example, be chosen from:

celluloses modified with groups comprising at least one fatty chain; for example: hydroxyethylcelluloses modified with groups comprising at least one fatty chain chosen from alkyl, alkenyl and alkylaryl groups;

(2) hydroxypropyl guars modified with groups comprising at least one fatty chain;

(3) polyether urethanes comprising at least one fatty chain, such as C8-C30 alkyl or alkenyl groups;

(4) copolymers of vinylpyrrolidone and of fatty-chain hydrophobic monomers;

(5) copolymers of C1-C6 alkyl acrylates or methacrylates and of amphiphilic monomers comprising at least one fatty chain;

(6) copolymers of hydrophilic acrylates or methacrylates and of hydrophobic monomers comprising at least one fatty chain.

The anionic amphiphilic polymers comprising at least one hydrophilic unit and at least one fatty-chain unit, may, for example, be chosen from those comprising at least one fatty-chain allyl ether unit and at least one hydrophilic unit comprising an ethylenic unsaturated anionic monomeric unit, for example, a vinylcarboxylic acid unit and further, for example, chosen from units derived from acrylic acids, methacrylic acids and mixtures thereof, wherein the fatty-chain allyl ether unit corresponds to the monomer of formula below:

$$CH_2=C(R_1)CH_2OB_nR \quad (I)$$

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

The anionic amphiphilic polymers may further be chosen, for example, from those comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid. The hydrophilic unit of unsaturated olefinic carboxylic acid type corresponds to, for example, the monomer of formula (II) below:

$$CH_2=C(R_1)COOH \quad (II)$$

in which R1 is chosen from H, CH3, C2H5 and CH2COOH, i.e. acrylic acid, methacrylic, ethacrylic and itaconic acid units. And the hydrophobic unit of the type such as a (C8-C30) alkyl ester or (C8-C30) oxyethylenated alkyl ester of an unsaturated carboxylic acid corresponds to, for example, the monomer of formula (III) below:

$$CH_2=C(R_1)COOB_nR_2 \quad (III)$$

in which R1 is chosen from H, CH3, C2H5 and CH2COOH (i.e. acrylate, methacrylate, ethacrylate and itaconate units), B is an ethyleneoxy radical, n is chosen from zero and integers ranging from 1 to 100, R2 is chosen from C8-C30 alkyl radicals, for example, C12-C22 alkyl radical.

Representative anionic amphiphilic polymers that can be used may further be cross-linked The crosslinking agent can be a monomer comprising a group (IV)

$$CH_2=C< \quad (IV)$$

with at least one other polymerizable group whose unsaturated bonds are not conjugated with respect to one another. Mention may be made, for example, of polyallyl ethers such as polyallylsucrose and polyallyl pentaerythritol.

The cationic amphiphilic polymers used are, for example, chosen from quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Among amphoteric amphiphilic polymers comprising at least one hydrophilic unit and at least one fatty-chain unit, mention may be made, for example, of methacrylamidopropyltrimethylammonium chloride/acrylic acid/C8-C30 alkyl methacrylate copolymers, wherein the alkyl radical is, for example, a stearyl radical.

Preferable associative polymeric thickeners for use herein comprise at least one hydrophilic unit which is unsaturated carboxylic acid or its derivative, and at least one hydrophobic unit which is a C8 to C30 alkyl ester or oxyethylenated C8-C30 alkyl ester of unsaturated carboxylic acid. The unsaturated carboxylic acid is preferably acrylic acid, methacrylic acid or itaconic acid. Examples can be made of material sold under trade name Aculy-22 by the company Rohm & Haas, materials sold under trade names Pemulen TR1 and Pemulen TR2, Carbopol 2020, Carbopol Ultrez-21 by the company Noveon, and materials sold under the trade names Structure 2001 and Structure 3001 by the company National Starch. Another preferable associative polymer for use in the polymer thickening systems of the present invention include polyether polyurethane, for example materials sold under the trade name Aculyn-44 and Aculyn-46 by the company Rohm and Haas. Another preferable associative polymer for use herein is cellulose modified with groups comprising at least one C8-C30 fatty chain, such as the product Natrosol Plus Grade 330 CS sold by the company Aqualon.

Non-associative cross-linked polycarboxylic polymers for use herein can be chosen, for example, from:
(i) cross-linked acrylic acid homopolymers;
(ii) copolymers of acrylic or (meth)acrylic acid and of C1-C6 alkyl acrylate or (meth)acrylate.

Preferable polymers are the products sold under the names Carbopol 980, 981, 954, 2984, 5984 by the company Noveon or the products sold under the names Synthalen M, Synthalen L and Synthalen K by the company 3V Sigma, or the product sold under the name Aculyn-33 by the company Rohm and Haas.

The polysaccharides for use herein are, for example, chosen from glucans, modified and unmodified starches (such as those derived, for example, from cereals, for instance wheat, corn or rice, from vegetables, for instance yellow pea, and tubers, for instance potato or cassaya), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and non-ionic derivatives thereof (hydroxypropyl guar) and bio-polysaccharides, such as xanthan gums, gellan gums, welan gums, scleroglucans, succinoglycans and mixtures thereof.

For example, suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums-Polysaccharides and their Derivatives", edited by Roy L. Whistler, Second Edition, published by Academic Press Inc., the content of these three publications being entirely incorporated by reference.

The polysaccharide is preferably a bio-polysaccharide, particulaly preferable are bio-polysaccharides selected from xanthan gum, gellan gum, welan gum, scleroglucan or succinoglycan, for example material sold under the name Keltrol® T by the company Kelco and the material sold by the name Rheozan® by the company Rhodia Chimie.

Another preferable polysaccharide is hydroxypropyl starch derivative, particularly preferable hydroxypropyl starch phosphate, for example the material sold under the name Structure XL® by the company National Starch.

Suitable for use herein are salt tolerant thickeners, including but not limited to: xanthan, guar, hydroxypropyl guar, scleroglucan, methyl cellulose, ethyl cellulose (available as AQUACOTE™), hydroxyethyl cellulose (NATROSOL™), carboxymethyl cellulose, hydroxypropylmethyl cellulose, microcrystalline cellulose, hydroxybutylmethyl cellulose, hydroxypropyl cellulose (available as KLUCEL™), hydroxyethyl ethyl cellulose, cetyl hydroxyethyl cellulose (available as NATROSOL™ Plus 330), N-vinylpyrollidone (available as POVIDONE™), Acrylates/Ceteth-20 Itaconate Copolymer (available as STRUCTURE™3001), hydroxypropyl starch phosphate (available as STRUCTURE™ ZEA), polyethoxylated urethanes or polycarbamyl polyglycol ester (e.g. PEG-150/Decyl/SMDI copolymer (available as ACULYN™ 44), PEG-150/Stearyl/SMDI copolymer (available as ACULYN™ 46), trihydroxystearin (available as THIXCIN™), acrylates copolymer (e.g. available as ACULYN™ 33) or hydrophobically modified acrylate copolymers (e.g. Acrylates/Steareth-20 Methacrylate Copolymer (available as ACULYN™ 22), acrylates/steareth-20 methacrylate crosspolymer (available as ACULYN™ 88), acrylates/vinyl neodecanoate crosspolymer (available as ACULYN™ 38), acrylates/beheneth-25 methacrylate copolymer (available as ACULYN™ 28), acrylates/C10-30 alkyl acrylate crosspolymer (available as Carbopol® ETD 2020), non-ionic amphophilic polymers comprising at least one fatty chain and at least one hydrophilic unit selected from polyether urethanes comprising at least one fatty chain, and blends of Ceteth-10 phosphate, Di-cetyl phosphate and Cetearyl alcohol (available as CRODAFOS™ CES).

Surfactants

The compositions according to the present invention may comprise one or more surfactants. Surfactants suitable for use herein generally have a lipophilic chain length of from about 8 to about 30 carbon atoms and can be selected from anionic, nonionic, amphoteric and cationic surfactants and mixtures thereof. The total level of surfactant is from about 1% to about 60%, preferably from about 2% to about 30%, more preferably from about 8% to about 25% and especially from about 10% to about 20% by weight.

The compositions of the invention preferably comprise a mixture of anionic and amphoteric surfactants with one or more nonionic surfactants. Anionic components, where may be present in the range of from about 0.1% to about 20%, preferably from about 0.1% to about 15%, and more preferably from about 5% to about 15% by weight of the composition; amphoteric or nonionic components, may independently be present is in the range from about 0.1% to about 15% by weight, preferably from about 0.5% to about 10%, more preferably from about 1% to about 8% by weight.

As examples of anionic surfactants, which can be used, alone or as mixtures, mention may be made, for example, of salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

The nonionic surfactants are compounds that are well known (see, for example, in this respect "Handbook of Surfactants" by M. R. Porter, published by Blackie & Son (Glasgow and London), 1991, pp. 116-178). They can be chosen, for example, from polyethoxylated, polypropoxylated and polyglycerolated fatty acids, alkyl phenols, α-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their momo-ethanolamine and diethanolamine derivatives, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

The amphoteric surfactants can be chosen, for example, from aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$) alkylamido($C_1$-$C_6$) alkylsulphobetaines.

Among the amine derivatives, mention may be made of the products sold under the name Miranol, as described, for example, in U.S. Pat. Nos. 2,528,378 and 2,781,354 and having the structures of: $R_2$—$CONHCH_2CH_2$—$N^+(R_3)(R_4)$($CH_2COO^-$), (VI) in which: $R_2$ is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group; and of $R_5$—$CONHCH_2CH_2$—$N(B)(C)$ (VII) wherein B represents $CH_2CH_2OX'$, C represents —($CH_2)_z$—Y', with z=1 or 2, X' is chosen from the —$CH_2CH_2$—COOH group and a hydrogen atom, Y' is chosen from —COOH and —$CH_2$ CHOH—$SO_3H$ radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{1-7}$ alkyl radical and its iso form, and unsaturated $C_{17}$ radical. These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid. Salts of diethyl aminopropyl cocoaspartamid can be also used.

The cationic surfactants may be chosen from: A) the quaternary ammonium salts of general formula (VIII) below:

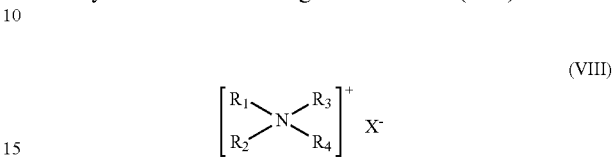

wherein $X^-$ is an anion chosen from halides (chloride, bromide and iodide), ($C_2$-$C_6$)alkyl sulphates, such as methyl sulphate, phosphates, alkyl and alkylaryl sulphonates, and anions derived from organic acids, such as acetate and lactate, and i) the radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals can comprise at least one hetero atom such as oxygen, nitrogen, sulphur and halogens. The aliphatic radicals are chosen, for example, from alkyl, alkoxy and alkylamide radicals, $R_4$ is chosen from linear and branched alkyl radicals comprising from 16 to 30 carbon atoms. The cationic surfactant is, for example, a behenyltrimethylammonium salt (for example chloride). ii) the radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals can comprise at least one hetero atom such as oxygen, nitrogen, sulphur and halogens. The aliphatic radicals are chosen, for example, from alkyl, alkoxy, alkylamide and hydroxyalkyl radicals comprising from about 1 to 4 carbon atoms; $R_3$ and $R_4$, which may be identical or different, are chosen from linear and branched alkyl radicals comprising from 12 to 30 carbon atoms, the said alkyl radicals comprise at least one function chosen from ester and amide functions. $R_3$ and $R_4$ are chosen, for example, from ($C_{12}$-$C_{22}$)alkylamido($C_2$-$C_6$) alkyl and ($C_{12}$-$C_{22}$) alkylacetate radicals. The cationic surfactant is, for example, a dicetyldimethyl ammonium salt (for example chloride);

B)—the quaternary ammonium salts of imidazolinium, such as that of formula (IX) below:

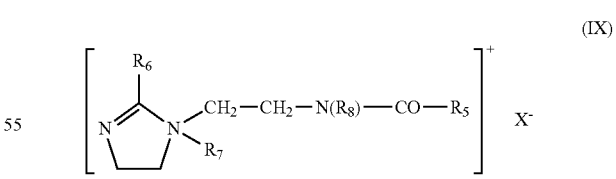

in which $R_5$ is chosen from alkenyl and alkyl radicals comprising from 8 to 30 carbon atoms, for example fatty acid derivatives of tallow, $R_6$ is chosen from a hydrogen atom, $C_1$-$C_4$ alkyl radicals and alkenyl and alkyl radicals comprising from 8 to 30 carbon atoms, $R_7$ is chosen from $C_1$-$C_4$ alkyl radicals, $R_8$ is chosen from a hydrogen atom and $C_1$-$C_4$ alkyl radicals, and $X^-$ is an anion chosen from halides, phosphates, acetates, lactates, alkyl sulphates, alkyl sulphonates and alkylaryl sulphonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), which are sold under the names "Rewoquat®" W75, W90, W75PG and W75HPG by the company Witco, C)—the diquaternary ammonium salts of formula (X):

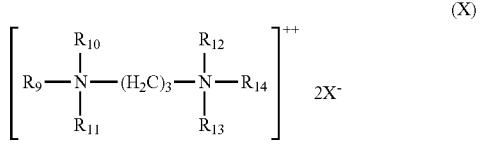

(X)

in which $R_9$ is chosen from aliphatic radicals comprising from about 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates. Such diquaternary ammonium salts, for example, include propanetallowediammonium dichloride; and D)—the quaternary ammonium salts comprising at least one ester function, of formula (XI) below:

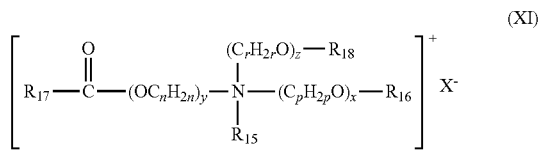

(XI)

in which: R15 is chosen from C1-C6 alkyl radicals and C1-C6 hydroxyalkyl and dihydroxyalkyl radicals; R16 is chosen from: a radical R19C(O)—, linear and branched, saturated and unsaturated C1-C22 hydrocarbon-based radicals R20, and a hydrogen atom, R18 is chosen from: a radical R21C(O)—, linear and branched, saturated and unsaturated C1-C6 hydrocarbon-based radicals R22, and a hydrogen atom, R17, R19 and R21, which may be identical or different, are chosen from linear and branched, saturated and unsaturated C7-C21 hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X— is an anion chosen from simple and complex, organic and inorganic anions; with the proviso that the sum x+y+z is from 1 to 15, that when x is 0, then R16 is R20 and that when z is 0, then R18 is R22.

In one embodiment, the ammonium salts of formula (XV) can be used, in which: R15 is chosen from methyl and ethyl radicals, x and y are equal to 1; z is equal to 0 or 1; n, p and r are equal to 2; R16 is chosen from: a radical R19C(O)—, methyl, ethyl and C14-C22 hydrocarbon-based radicals, and a hydrogen atom; R17, R19 and R21, which may be identical or different, are chosen from linear and branched, saturated and unsaturated C7-C21, hydrocarbon-based radicals; R18 is chosen from: a radical R21C(O)— and a hydrogen atom. Such compounds are sold, for example, under the names Dehyquart by the company Cognis, Stepanquat by the company Stepan, Noxamium by the company Ceca, and Rewoquat WE 18 by the company Rewo-Witco.

Method of Use

The hair colorant compositions usually are sold in kits comprising, in individually packaged components such as separate containers, a tint composition (also called "dye cream" for emulsions or "dye liquid" for solutions) comprising the oxidative dye precursors and an optional alkalizing agent in a suitable carrier, and; a oxidizing composition (also called "hydrogen peroxide cream" for emulsions or "hydrogen peroxide liquid" for solutions) comprising the oxidizing agent. The consumer mixes the tint composition and oxidizing composition together immediately before use to form a hair coloring composition and applies the hair coloring composition on to the hair. An alternative embodiment wherein the tint composition is provided in a solid form and mixed with a liquid oxidizing composition prior to application to the hair may also be utilized.

The tint and oxidizing compostions may be, independently from one another, prepared as so called thin liquids or creams. Typically thin type liquids have a viscosity of less than 1000cPs. Upon mixing the component parts, the resultant hair colouring or bleaching compositions preferably have a viscosity of from 1000 to 60000 cPs, more preferably from 2000 to 30000 cPs and most preferably from 3000 to 25000 cPs. Viscosity is measured using Brookfield viscometers with cone and plate attachment. For viscosities in the range of 0-12000 cPs the Brookfield DV-11 viscometer with S42 plate is used. 2 ml sample of the composition is equilibrated at 26.7° C. for three minutes before the readings are taken at 1 rpm. For viscosities in the range of 12,000-60,000 cPs the Brookfield DV-1 viscometer with S52 plate is used. 0.5 ml sample of the composition is equilibrated for 1 minute at 26.7° C. before the readings are taken at 1 rpm.

Application of the hair colorant composition to the hair may be undertaken in several ways. Application of the hair colorant composition may take place on the whole head of hair of an end user. By "whole head of hair" is it meant that the hair all over the head from the root of the hair to the tip of the hair is included. By contrast, the application of the hair colorant composition may take place on the root portion of the hair. The application to the root portion of the hair may still be over the entire head of the end user, but application of the hair colorant composition is applied only to the section of hair closest to the head (root portion), which is between about 0.01 mm to about 4 mm from the scalp of the head. Also, application may take place on a portion of hair. Application of a portion of hair is commonly referred to as highlighting or lowlighting. The portion of hair may be physically separated from the whole head of hair in a hair bundle or may be a smaller portion of hair than the whole head of hair. A hair bundle may be physically separated from a whole head of hair by a device including a plastic cap through which hair bundles are formed when hair is pulled through orifices in the plastic cap, metal foils encompassing a hair bundle, strand separators applied to hair at the root portion, or similar devices.

When present, an optional conditioning agent can be provided in a third container. In the latter case, all three compositions can be mixed immediately before use and applied together, or the content of the third container can be applied (after an optional rinse step) as a post-treatment immediately after the hair colorant composition.

According to one method for oxidatively coloring hair, the method comprises mixing a tint composition and an oxidizing composition together to form a hair colorant composition, applying a hair colorant composition to the hair, waiting for a period of 5-45 minutes, such as 20-30 minutes, and then removing the hair colorant composition from the hair.

The methods of coloring hair also may further comprise working the hair colorant composition into the hair by hand or by a tool for a few minutes to ensure uniform application to all of the hair. The hair colorant composition remains on the hair while the end hair color develops for a time period of 5 to 45 minutes. The consumer then rinses his/her hair thoroughly with tap water and allows it to dry and/or styles the hair.

Kits comprising one container for the first composition (tint composition) and one container for the second composition (oxidizing composition) can be advantageously used for this method. Optionally, a third composition may comprise an alkaline agent, such as monoethanolamine (MEA). The kit further comprises instructions for mixing and application of the hair colorant composition. The kit may further include an object such as a mixing bowl, an application device, a dispensing device, gloves, hair strand separators, and any combination of these objects. The kit also may comprise an additional container for a composition comprising a conditioning agent.

In one embodiment, the hair coloring kit may comprise (i) an individually packaged oxidizing composition comprising an oxidizing agent; and (ii) an individually packaged tint composition.

The individually packaged tint composition may comprise: (a) a first coupler consisting of 3-amino-2,6-dimethylphenol; (b) a second coupler selected from the group consisting of 2,6-dihydroxyethylaminotoluene, 2,6-diaminopyridine, cosmetically acceptable salts of any of these, and mixtures of at least two of these; and (c) a developer selected from the group consisting of 2-methyl-1,4-benzenediamine (PTD); 2-methyl-1,4-benzenediamine sulfate salt (DTS); p-phenylenediamine (PPD); hydroxyethyl-p-phenylenediamine; N,N-bis(hydroxyethyl)-p-phenylenediamine; 2-methoxymethyl-1,4-benzenediamine (MBB), cosmetically acceptable salts of any of these, and mixtures comprising at least two of these. The oxidizing agent may be selected from any of the oxidizing agents described above such as, for example, hydrogen peroxide, inorganic or organic alkali-metal peroxides, per salts, inorganic perhydrate salts, alkyl or aryl peroxides or peroxidases, percarbonates, persulfates, peroxymonocarbonates. Optionally, the tint composition may comprise an alkalizing agent such as ammonia and ammonium salts and alkanolamines and their salts.

The hair colorant compositions may be used in a variety of packaging and dispensing devices. These dispensing devices can come in the form of separate devices that may be used independently or in combination with one another. Typically, the hair colorant compositions are contained within separate single-compartment or multi-compartment containers such that the tint composition and oxidizing composition can be stored separately from one another before use. The tint composition and the oxidizing composition then are mixed together in a mixing bowl or in a dispensing device (such as a squeeze bottle, a squeeze foamer, pump foamer, and the like) and then applied to the consumer's hair via a tool (brush, comb, or the like) or by hand after dispensed from the dispensing device.

The most common packaging device involves storing the oxidizing composition in a container such as a bottle, tube, squeeze foamer, pump foamer or a sachet and separately storing the tint composition in an additional package such as a bottle, tube or sachet.

EXAMPLES

Hair colorant compositions tested were formulated by mixing a tint composition according to the formulation below in TABLE 1 with an oxidizing component in a 1:1 ratio. The oxidizing component is a commercially available WELLOXON® developer at 6% (20 vol) peroxide concentration. In all the tests, a hair tress (white, brown and mixed black/grey tresses) was used (1.5 g tresses).

To each tress, 3 g of the tint composition and 3 g of the oxidizing composition were applied for 30 minutes at 30° C. The tresses were rinsed for 2 minutes, including 30 seconds shampoo.

TABLE 1

Example Tint Component Formulations

| Ingredient | Amount (wt. %) |
| --- | --- |
| Oleic diethanolamide | 12.0 |
| Oleic Acid | 5.0 |
| Propylene Glycol | 3.5 |
| Ethanol | 7.0 |
| Dipropylene Glycol | 0.5 |
| Propylene Glycol Methyl ether | 9.0 |
| Sodium Sulfite | 0.159 |
| Ammonia (28%) | 7.140 |
| Ammonium Acetate | 0.8 |
| EDTA | 0.05 |
| Erythorbic acid | 0.4 |
| 3-amino-2,6-dimethylphenol | 0.343 |
| Second Coupler[1] | 0.338 |
| DTS | 1.101 |
| Fragrance | 1.000 |
| Reverse-osmosis water | QS to 100% |

[1]Selected from compounds of formulas (IIA)-(IIB)

A swatch of white hair may be used to ascertain a color value of the hair colorant composition. Perceived color benefit may be further noticeable from the characteristics of the two additional swatches. After the hair is rinsed and dried, the color of the tress is measured using a 3700d Minolta Spectrophotometer.

Data from the spectrophotometer provide coordinates for both L*a*b* and LCh color spaces. In both the L*a*b* and LCh color spaces, the L* value refers to lightness on a scale of zero to 100, with lower values indicating a darker color. In the L*a*b* color space, the coordinate a* designates a position between red and green, with higher numbers indicating a redder shade and lower numbers representing a greener shade. The coordinate b* designates a position between yellow and blue, with higher numbers indicating a yellower shade and lower numbers representing a bluer shade. In the LCh color space, the value C represents chroma, with higher values indicating a deeper, brighter color and lower values indicating a less deep, duller color. The value C in the LCh space is related to a* and b* in the L*a*b* space by the relationship $C=[(a^*)^2+(b^*)^2]^{1/2}$. The coordinate h in the LCh space represents hue angle, in which colors are represented as degree values from 0° to 360°.

Differences between the hair colorant compositions containing MeAHT and the comparative hair colorant compositions containing AHT are determined from the L*, a*, b*, and C and h values, such that a negative value for any of ΔL*, Δa*, Δb*, and ΔC represents a lower value in hair colorant compositions containing MeAHT than in hair colorant compositions containing AHT. Color data for the hair colorant compositions prepared as described are summarized in TABLES 2-4.

TABLE 2

Comparative color data on white hair swatches from hair colorant compositions comprising MeAHT coupler combinations vs. comparative AHT combinations

| Example | Second Coupler | L* | a* | b* | C* | h |
|---|---|---|---|---|---|---|
| 2,6-dihydroxyethylaminotoluene + DTS + Second Coupler | | | | | | |
| Example 3 | MeAHT | 18.49 | 16.16 | −5.94 | 17.21 | 339.82 |
| Comparative Example 3 | AHT | 17.68 | 13.93 | −6.01 | 15.17 | 336.65 |
| Δ(MeAHT − AHT) | | +0.81 | +2.23 | +0.07 | +2.04 | +3.17 |
| 2,6-diaminopyridine + DTS + Second Coupler | | | | | | |
| Example 4 | MeAHT | 16.93 | 2.99 | −5.94 | 6.65 | 296.75 |
| Comparative Example 4 | AHT | 16.81 | 1.64 | −6.17 | 6.39 | 284.84 |
| Δ(MeAHT − AHT) | | +0.12 | +1.35 | +0.23 | +0.26 | +11.91 |

TABLE 3

Comparative color data on brown hair swatches from hair colorant compositions comprising MeAHT coupler combinations vs. comparative AHT combinations

| Example | Second Coupler | L* | a* | b* | C* | h |
|---|---|---|---|---|---|---|
| 2,6-dihydroxyethylaminotoluene + DTS + Second Coupler | | | | | | |
| Example 9 | MeAHT | 17.31 | 12.22 | −2.59 | 12.49 | 348.03 |
| Comparative Example 9 | AHT | 17.43 | 9.91 | −2.53 | 10.23 | 345.65 |
| Δ(MeAHT − AHT) | | −0.12 | +2.31 | −0.06 | +2.26 | +2.38 |
| 2,6-diaminopyridine + DTS + Second Coupler | | | | | | |
| Example 10 | MeAHT | 16.52 | 1.50 | −2.84 | 3.21 | 297.78 |
| Comparative Example 10 | AHT | 17.10 | 0.32 | −3.63 | 3.64 | 275.02 |
| Δ(MeAHT − AHT) | | −0.58 | +1.18 | +0.79 | −0.43 | +22.76 |

TABLE 4

Comparative color data on 50% blended-gray hair swatches from hair colorant compositions comprising MeAHT coupler combinations vs. comparative AHT combinations

| Example | Second Coupler | L* | a* | b* | C* | h |
|---|---|---|---|---|---|---|
| 2,6-dihydroxyethylaminotoluene + DTS + Second Coupler | | | | | | |
| Example 15 | MeAHT | 17.05 | 11.00 | −5.04 | 12.10 | 335.38 |
| Comparative Example 15 | AHT | 16.82 | 10.44 | −5.36 | 11.74 | 332.82 |
| Δ(MeAHT − AHT) | | +0.23 | +0.56 | +0.32 | +0.36 | +2.56 |
| 2,6-diaminopyridine + DTS + Second Coupler | | | | | | |
| Example 16 | MeAHT | 17.03 | 2.13 | −4.49 | 4.97 | 295.36 |
| Comparative Example 16 | AHT | 17.62 | 1.11 | −5.66 | 5.77 | 281.14 |
| Δ(MeAHT − AHT) | | −0.59 | +1.02 | +1.17 | −0.80 | +14.22 |

According to the color data in TABLE 2, on the white hair, each oxidative hair colorant composition containing MeAHT exhibited a significantly higher value for Δa*, indicating a color benefit with respect to increased red shade. The color data in TABLE 3 for brown hair were consistent the data from the white hair, in that the samples generally showed a color benefit arising from an increased red shade. The color data in TABLE 4 from the 50% blended gray hair also showed a substantial color benefit in the compositions containing MeAHT. Though the color benefit varied across the formulations on different hair colors, it will be understood that, in general, hair colorant formulations may be tailored for use on specific consumer hair colors. As such, a notable figure of merit with regard to color benefit is realization of the color benefit on at least one type of hair, not necessarily on all types of hair.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

The term "independently selected from," as used in the specification and appended claims, is intended to mean that the referenced groups can be the same, different, or a mixture thereof, unless the context clearly indicates otherwise. Thus, under this definition, the phrase "$X^1$, $X^2$, and $X^3$ are independently selected from noble gases" would include the scenario where $X^1$, $X^2$, and $X^3$ are all the same, where $X^1$, $X^2$, and $X^3$ are all different, and where $X^1$ and $X^2$ are the same but $X^3$ is different.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

Though particular embodiments have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair colorant composition comprising:
   (a) a first dye coupler consisting of 3-amino-2,6-dimethylphenol;
   (b) a second dye coupler selected from the group consisting of 2,6-dihydroxyethylaminotoluene, 2,6-diaminopyridine, cosmetically acceptable salts of any of these, and mixtures of at least two of these;
   (c) a developer selected from the group consisting of 2-methyl-1,4-benzenediamine, 2-methyl-1,4-benzenediamine sulfate salt, p-phenylenediamine, hydroxyethyl-p-phenylenediamine, N,N-bis(hydroxyethyl)-p-phenylenediamine, 2-methoxymethyl-1,4-benzenediamine, cosmetically acceptable salts of any of these, and mixtures of at least two of these; and
   (d) an oxidizing agent.

2. The hair colorant composition of claim 1, wherein said developer is 2-methylbenzene-1,4-diamine or a cosmetically acceptable salt thereof.

3. The hair colorant composition of claim 1, wherein said developer is 2-methylbenzene-1,4-diamine sulfate salt.

4. The hair colorant composition of claim 1, wherein said oxidative hair colorant composition is devoid of 5-amino-2-methylphenol.

5. The hair colorant composition of claim 1, comprising by weight, based on the weight of the hair colorant composition:
from about 0.001% to about 6% of said first dye coupler;
from about 0.001% to about 6% of said second dye coupler;
from about 0.001% to about 6% of said developer; and
from 0.1% to 10% of said oxidizing agent.

6. The hair colorant composition of claim 1, wherein said oxidizing agent is selected from the group consisting of hydrogen peroxide, inorganic or organic alkali-metal peroxides, per salts, inorganic perhydrate salts, alkyl or aryl peroxides or peroxidases, oxidases, uricases, percarbonates, persulfates, peroxymonocarbonates, and mixtures thereof.

7. The hair colorant composition of claim 6, comprising by weight, based on the weight of the hair colorant composition, a total of from about 0.001% to about 6% of said developer, said first dye coupler, and said second dye coupler.

8. The hair colorant composition of claim 1, further comprising an alkalizing agent.

9. A method of treating hair, said method comprising:
(i) providing a tint composition comprising:
  (a) a first dye coupler consisting of 3-amino-2,6-dimethylphenol;
  (b) a second dye coupler selected from the group consisting of 2,6-dihydroxyethylaminotoluene, 2,6-diaminopyridine, cosmetically acceptable salts of any of these, and mixtures of at least two of these; and
  (c) a developer selected from the group consisting of 2-methyl-1,4-benzenediamine, 2-methyl-1,4-benzenediamine sulfate salt, p-phenylenediamine, p-toluenediamine, hydroxyethyl-p-phenylenediamine, N,N-bis(hydroxyethyl)-p-phenylenediamine, 2-methoxymethyl-1,4-benzenediamine, cosmetically acceptable salts of any of these, and mixtures of at least two of these;
(ii) adding to said tint composition an oxidizing composition comprising an oxidizing agent to form a hair coloring composition;
(iii) contacting said hair with said hair coloring composition.

10. The method of claim 9, further comprising separating a hair bundle from said hair, wherein said contacting of said hair comprises contacting said hair bundle with said hair coloring composition.

11. The method of claim 9, wherein said hair is selected from the group consisting of a whole head of said hair, a root portion of hair, and a hair bundle separated from a whole head of hair.

12. A hair coloring kit comprising:
(i) an individually packaged oxidizing composition comprising an oxidizing agent;
(ii) an individually packaged tint composition comprising:
  (a) a first dye coupler consisting of 3-amino-2,6-dimethylphenol;
  (b) a second dye coupler selected from the group consisting of 2,6-dihydroxyethylaminotoluene, 2,6-diaminopyridine, cosmetically acceptable salts of any of these, and mixtures of at least two of these; and
  (c) a developer selected from the group consisting of 2-methyl-1,4-benzenediamine, 2-methyl-1,4-benzenediamine sulfate salt, p-phenylenediamine, p-toluenediamine, hydroxyethyl-p-phenylenediamine, N,N-bis(hydroxyethyl)-p-phenylenediamine, 2-methoxymethyl-1,4-benzenediamine, cosmetically acceptable salts of any of these, and mixtures of at least two of these.

13. The hair coloring kit of claim 12, further comprising instructions for forming a hair coloring composition from the oxidizing composition and the tint composition.

14. The hair coloring kit of claim 12, further comprising instructions for contacting hair with the hair coloring composition.

15. The hair coloring kit of claim 12, further comprising an object selected from the group consisting of a mixing bowl, an application device, a dispensing device, gloves, hair-strand separators, and combinations thereof.

16. The hair coloring kit of claim 12, wherein said oxidizing agent is selected from the group consisting of hydrogen peroxide, inorganic or organic alkali-metal peroxides, per salts, inorganic perhydrate salts, alkyl or aryl peroxides or peroxidases, oxidases, uricases, percarbonates, persulfates, peroxymonocarbonates, and mixtures thereof.

17. The hair coloring kit of claim 12 wherein said tint composition further comprises an alkalizing agent.

\* \* \* \* \*